United States Patent
Prescott

(10) Patent No.: US 7,117,870 B2
(45) Date of Patent: Oct. 10, 2006

(54) LACRIMAL INSERT HAVING RESERVOIR WITH CONTROLLED RELEASE OF MEDICATION AND METHOD OF MANUFACTURING THE SAME

(75) Inventor: Anthony D. Prescott, Arlington, TN (US)

(73) Assignee: Clarity Corporation, Memphis, TN (US)

( * ) Notice: Subject to any disclaimer, the term of this patent is extended or adjusted under 35 U.S.C. 154(b) by 106 days.

(21) Appl. No.: 10/899,416

(22) Filed: Jul. 26, 2004

(65) Prior Publication Data

US 2006/0020248 A1    Jan. 26, 2006

(51) Int. Cl.
 *A61B 19/00* (2006.01)
 *A61M 35/00* (2006.01)
 *A61K 9/22* (2006.01)
 *A61F 13/00* (2006.01)
 *B65B 3/02* (2006.01)

(52) U.S. Cl. ............... 128/898; 604/294; 604/891.1; 424/424; 53/452

(58) Field of Classification Search ............... 604/294, 604/298, 891.1, 892.1; 424/427, 428, 424; 53/473; 128/898; 600/33, 34, 35
 See application file for complete search history.

(56) References Cited

U.S. PATENT DOCUMENTS

| | | | |
|---|---|---|---|
| 2,199,210 A * | 4/1940 | Scherer ...................... 53/451 |
| 3,453,797 A * | 7/1969 | Soto ............................ 53/411 |
| 3,710,795 A * | 1/1973 | Higuchi et al. ............. 424/424 |
| 3,760,984 A * | 9/1973 | Theeuwes ................... 222/95 |
| 3,811,443 A * | 5/1974 | Dickinson et al. ........... 600/35 |
| 3,949,750 A | 4/1976 | Freeman .................... 128/260 |
| 3,967,618 A * | 7/1976 | Zaffaroni ................... 128/833 |
| 3,993,071 A | 11/1976 | Higuchi et al. |
| 3,993,073 A * | 11/1976 | Zaffaroni .................... 424/424 |
| 4,001,388 A | 1/1977 | Shell ........................... 424/14 |
| 4,014,335 A | 3/1977 | Arnold |
| 4,300,557 A * | 11/1981 | Refojo et al. ............... 424/424 |
| 4,313,904 A * | 2/1982 | Larkin et al. ............... 264/515 |
| 4,343,787 A | 8/1982 | Katz |
| 4,863,457 A * | 9/1989 | Lee .......................... 604/891.1 |
| 4,973,304 A * | 11/1990 | Graham et al. ............... 604/48 |
| 5,006,117 A * | 4/1991 | Cassou ...................... 604/403 |
| 5,174,999 A * | 12/1992 | Magruder et al. .......... 424/423 |
| 5,378,475 A * | 1/1995 | Smith et al. ................ 424/473 |
| 5,423,777 A * | 6/1995 | Tajiri et al. ................. 604/294 |
| 5,466,233 A * | 11/1995 | Weiner et al. ............ 604/890.1 |
| 5,536,243 A * | 7/1996 | Jeyendran .................... 600/35 |
| 5,725,493 A * | 3/1998 | Avery et al. ................ 604/294 |
| 5,766,242 A * | 6/1998 | Wong et al. ................ 128/898 |
| 5,795,591 A * | 8/1998 | Lee et al. ................... 424/473 |
| 5,840,054 A | 11/1998 | Hamano et al. |

(Continued)

*Primary Examiner*—Tatyana Zalukaeva
*Assistant Examiner*—Paula L. Craig
(74) *Attorney, Agent, or Firm*—Gordon & Jacobson, P.C.

(57) ABSTRACT

A lacrimal insert includes a body defining a reservoir, and a head provided at an end of the body and closing the reservoir. The body is made from a material impermeable to the medication while the head is made from a permeable material adapted to release the medication from the reservoir to the eye at a determinable rate. In one manufacture, the body of the insert is molded and includes a hole at a tip end; the head is molded onto the body; the medication is injected into the insert through the tip end hole; and the tip end is sealed. The portion of the insert at which the medication is released is precisely fabricated in order to control release of the medication, and the reservoir is filled and then closed away from the area of medication permeability.

12 Claims, 5 Drawing Sheets

U.S. PATENT DOCUMENTS

| | | | |
|---|---|---|---|
| 5,861,166 A * | 1/1999 | Eckenhoff | 424/422 |
| 5,928,662 A * | 7/1999 | Phillips | 424/427 |
| 6,042,909 A * | 3/2000 | Dunleavy et al. | 428/35.7 |
| 6,113,938 A * | 9/2000 | Chen et al. | 424/423 |
| 6,196,993 B1 | 3/2001 | Cohan et al. | 604/89.1 |
| 6,331,313 B1 * | 12/2001 | Wong et al. | 424/427 |
| 6,375,972 B1 * | 4/2002 | Guo et al. | 424/423 |
| 6,719,750 B1 * | 4/2004 | Varner et al. | 604/289 |
| 6,756,058 B1 * | 6/2004 | Brubaker et al. | 424/473 |
| 2001/0027301 A1 * | 10/2001 | Lau et al. | 604/310 |
| 2003/0014036 A1 * | 1/2003 | Varner et al. | 604/521 |
| 2004/0176341 A1 * | 9/2004 | Chou et al. | 514/179 |
| 2004/0230183 A1 * | 11/2004 | Breegi et al. | 604/891.1 |

* cited by examiner

LACRIMAL INSERT HAVING RESERVOIR WITH CONTROLLED RELEASE OF MEDICATION AND METHOD OF MANUFACTURING THE SAME

BACKGROUND OF THE INVENTION

1. Field of the Invention

This invention relates broadly to ophthalmic devices, and particularly to a lacrimal insert preferably in the shape of a punctum plug. More particularly, this invention relates to lacrimal inserts adapted to store and release medication.

2. State of the Art

In order to treat various conditions, drugs are administered to the eye. The most common form of drug delivery is by topical application to the eye's surface, e.g., by drops. The eye is uniquely suited to surface administration because drugs can penetrate through the cornea, rise to therapeutic concentration levels inside the eye, and exert their beneficial effects. In fact, ninety five percent of drugs delivered to the eye are currently administered through eye drops. Rarely are drugs for the eye administered orally or by injection, either because they reach the eye in too low a concentration to have the desired pharmacological effect, or because their use is complicated by significant systemic side effects.

Topical eye drops, though effective, are inefficient. When an eye drop is instilled in the eye, it overfills the conjunctival sac, the pocket between the eye and the lids, causing a substantial portion of the drop to be lost due to overflow of the lid margin onto the cheek. In addition, a substantial portion of the drop remaining on the ocular surface is washed away into the nasolacrimal duct, thereby diluting the concentration of the drug. Not only is this portion of the drug dose lost before it can cross the cornea, but this excess drug may be undesirably carried into the nose and throat where it is absorbed into the local or general circulation, sometimes leading to serious systemic side effects. The small portion of the drug in the eye drop which does penetrate the cornea results in an initial peak tissue concentration, a higher level than is required for the initial pharmacological effect. The tissue concentration then gradually decreases, such that by the time the next eye drop is due, the tissue concentration and the intended pharmacological effect may be too low.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Therefore, sometimes one or more drops miss the eye. Older patients may have additional problems instilling drops due to arthritis, unsteadiness, and decreased vision, and pediatric and psychiatric patient populations pose difficulties as well.

As a result of the above problems, there have been efforts to use a punctum plug in a manner which optimizes topical administration to take advantage of the benefits of topical administration but overcomes its drawbacks. U.S. Pat. No. 3,949,750 to Freeman describes a lacrimal insert in the shape of a punctum plug manufactured of a porous material which stores and slowly dispenses an ophthalmic medication to the eye. The Freeman plug overcomes many of the negative of topical administration, as a large proportion of the slowly dispensed medication is subject to a level rate of uptake at the eye without overflow of the conjunctival sac. If there is any drawback to the Freeman plug, it is that the dose of medication which can be stored in a solid porous plug is relatively small.

U.S. Pat. No. 6,196,993 to Cohan et al. describes a punctum plug having a reservoir within the body of the plug adapted for storing a larger quantity of medication, and a collarette having a pore in communication with the reservoir. The reservoir has a closed lower end and an upper portion open to the pore. The medication stored in the reservoir is released through the pore to the surface of the eye over time, with pore size adapted to control release rate of the medication. In one embodiment, a medication-permeable material is provided over the pore. The plug itself is shown manufactured in the patent in one piece from silicone or another material that is impermeable to the medication. However, with the reservoir being larger than the upper pore, the Cohan device cannot be manufactured as a one-piece plug. In fact, early versions of the Cohan device were manufactured with the collarette being glued or otherwise fused to a neck portion of the plug and the medication then inserted into the reservoir through the pore. This construction has serious drawbacks. Drug release or permeability is affected by locating the gluing site of the collarette to the body adjacent the pore site, as the pore may become clogged with glue or otherwise impede movement of the medication so as to affect drug release. In addition, if the permeable membrane is desired to be used over the pore, it must be placed over the collarette after filling the reservoir through the pore, which creates difficulties in product handling as the placement of such membrane may cause inadvertent premature release of medication during handling. Furthermore, any adhesive used to attach the permeable membrane to the collarette may affect the release rate of medication during implantation.

SUMMARY OF THE INVENTION

It is therefore an object of the invention to provide an ophthalmological device for lacrimal insertion which includes a reservoir for a medication, which is adapted to release the medication over a period of time, and which is relatively easy to manufacture.

In accord with these objects, which will be discussed in detail below, a lacrimal insert is provided with a reservoir for storing a medication, such as a glaucoma, antimicrobial, anti-inflammatory, dry-eye syndrome medication and which, for purposes herein, shall also include a therapeutic such as a mydriatic or a cycloplegic. In one embodiment, the lacrimal insert is a punctum plug comprising a body having a neck end, a tip end and a centrally defined reservoir, and a head provided at the neck end of the body and enclosing the reservoir. The body is made from a first material which is substantially impermeable to the medication while the head is made from a second material which is permeable to the medication and adapted to release the medication from the reservoir to the eye at a determinable rate.

In accord with a preferred method of manufacturing the lacrimal insert of the invention, in a first step, the body is molded from the first material to define the reservoir. The internal space defining the reservoir is molded open at both the neck and tip ends. In a second step, the head is molded from the second material onto the neck end of the body. In a third step, the medication is injected into the reservoir of the plug through the tip end opening of the body. In a fourth step, the open tip end of the body is provided with a cork-like seal to close the reservoir. Thus, in accord with the invention, the reservoir is sealed at a location away from the area of medication permeability.

In accord with another embodiment of manufacture, where a self-healing material is used to mold the body, the body is molded with an internal space open only at the neck end. The head is then attached to the body prior to filing with medication. Thereafter, a needle is punctured through the body to inject the medication and then withdrawn, with the body self-healing to retain the medication.

In accord with yet another embodiment of the invention, a lacrimal insert design is provided which is adapted to release medication into the lacrimal duct, e.g., sinus or throat medications as opposed to at the ocular surface. The body is molded of a first relatively impermeable material with head, neck and a flared portions. The head portion defines an opening for injecting a medication. A tip molded of a second relatively more permeable material is then provided at the end of the flared portion. Medication is injected into the body to fill a reservoir defined between the body and tip, and a seal is then provided in the opening in the head portion to close the reservoir.

In accord with all embodiments of the invention, the first and second materials are preferably two types of silicone, one relatively impermeable to the medication, and the other having a suitable rate of permeability for the medication.

It will be appreciated that in accord with the invention, the portion of the insert at which the medication is released is precisely fabricated in order to control release of the medication, and the reservoir is filled and then closed away from the area of permeability.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
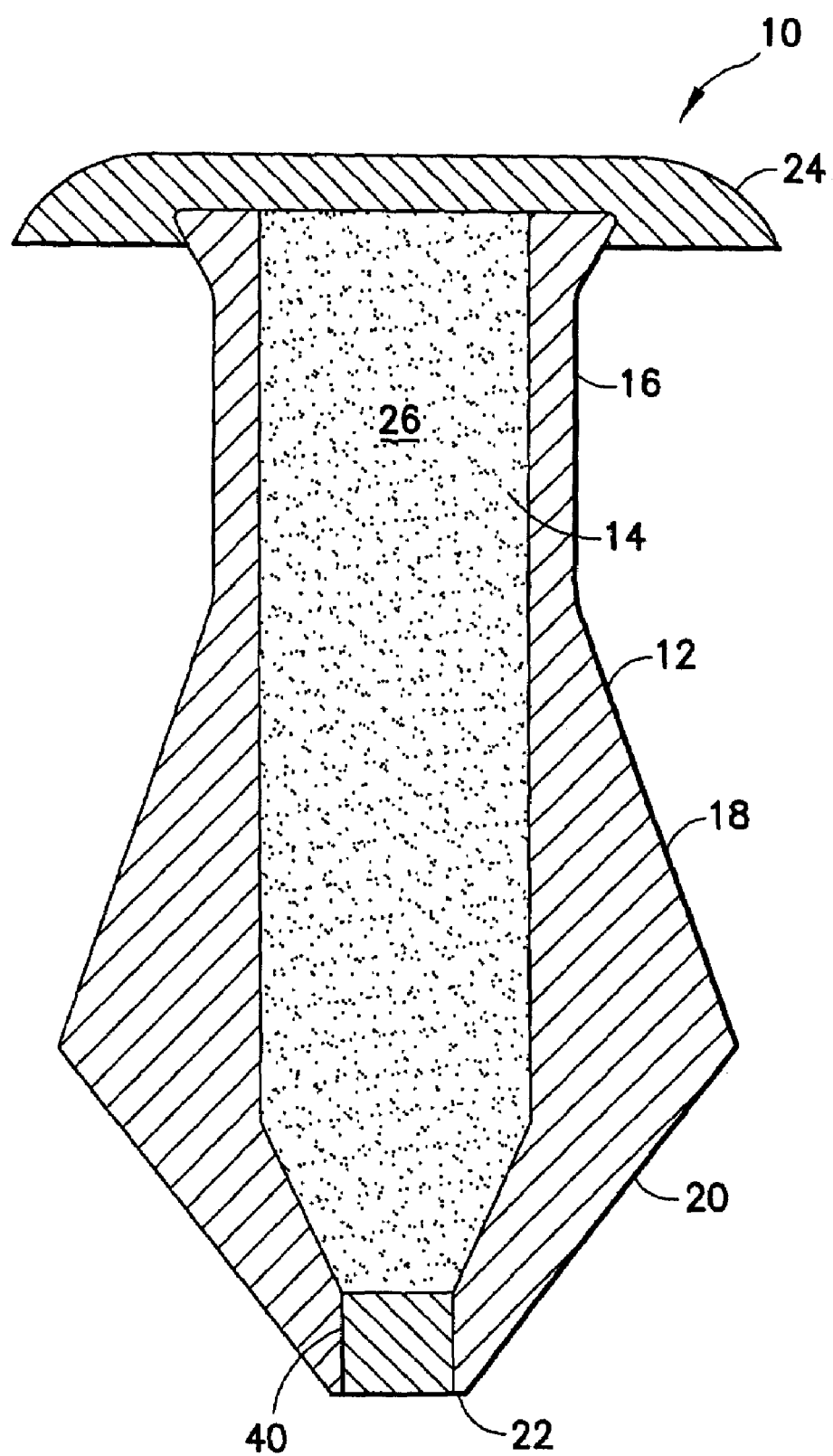
FIG. 1 is a schematic section view of a punctum plug according to a first embodiment of the invention.

Turning now to FIG. 1, a first embodiment of a lacrimal insert in the shape of a punctum plug 10 for insertion into a lacrimal puncta is shown. The punctum plug 10 includes a body 12 defining a reservoir 14, a neck portion 16, a flared portion 18, and a tapered portion 20 terminating in a tip 22. A non-porous head 24 is provided over the neck portion 16 of the body 12 and encloses the reservoir. A medication 26 is provided in the reservoir. In accord with one aspect of the invention, the body 12 and head 24 are made of different materials, with the body 12 being made from a biocompatible, preferably soft and flexible first material which is relatively impermeable to the medication, and the head 24 being made from a biocompatible, preferably soft and flexible second material which is permeable to the medication. Most preferably, both materials are silicones. Such silicones of selective permeability are available from NuSil Technology of Carpinteria, Calif. Other suitable materials may also be used. Materials may be selected to affect the rate of release of medication through the head 24 of the plug 10 (or other plug location, as discussed below with respect to FIGS. 8 through 10). Thus, the second material is preferably chosen for its desired rate of release with respect to a particular medication.

Figure 2:
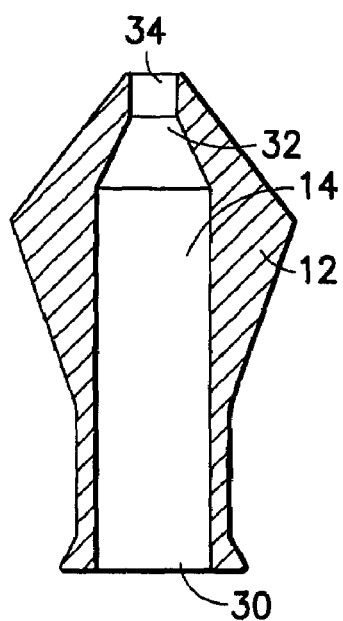
FIGS. 2 through 5 illustrate a method of manufacturing the punctum plug of FIG. 1.
Figure 3:
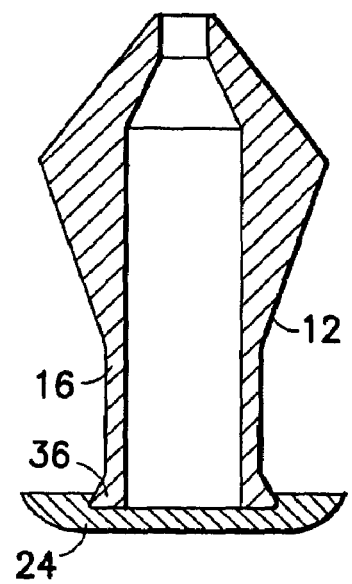
Figure 4:
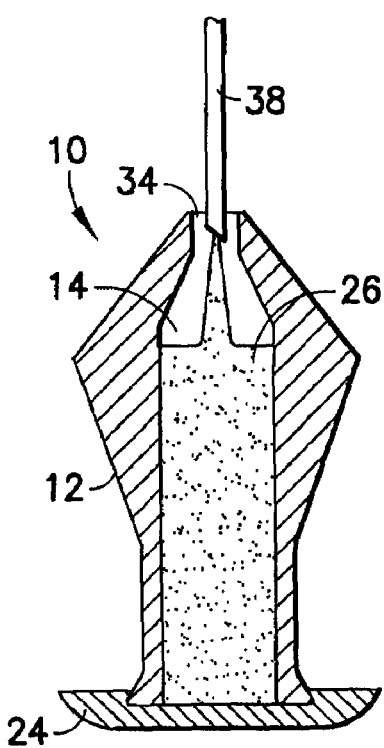
Figure 5:
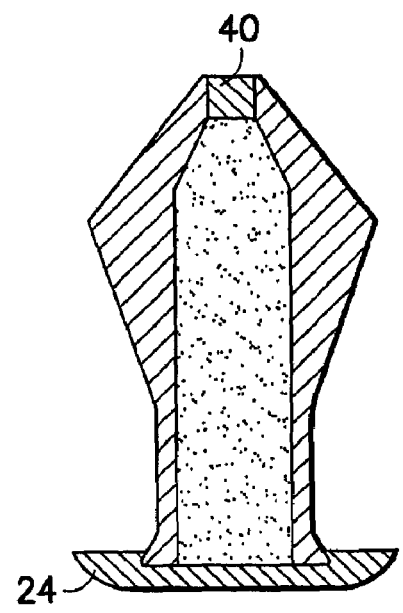

Referring to FIG. 2, in accord with a preferred method of manufacturing the plug 10, in a first step, the body 12 is molded from the first material to define the reservoir 14 having a larger diameter neck end 30, a tapered portion 32 and an open tip 34. Thus, the internal space defining the reservoir is molded open at both the neck and tip ends. Referring to FIG. 2, once the body has solidified, the head 24 is molded from the second material onto the neck portion 16 of the body 12. The end of the neck portion 16 may be provided with a flare 36 to facilitate molded engagement with the head 24. Referring to FIG. 3, after the head 24 has solidified onto the body 12 such that the body and head are integrated, the medication 26 is injected with a needle 38 or other suitable device into the reservoir 14 of the plug 10 through the open tip 34. Referring to FIG. 4, in a final step, the open tip 34 of the body 12 is sealed. In a preferred embodiment, a medication impermeable stopper 40 is provided to close the reservoir 14. The stopper 40 is preferably made of silicone or PTFE, though other suitable materials can be used. Alternatively, or additionally, a sealant may be 'painted' onto the plug at the site of the opening to provide the seal. Therefore, in accord with the invention, the reservoir 14 is sealed at a location away from the area of medication permeability, and most preferably at a location opposite the head 24. Thus, the portion of the plug at which the medication is released is precisely fabricated in order to control medication release, and the medication reservoir is closed away from the area of permeability so as not to interfere with such permeability.

The plug 10 is sized for insertion into a portion of the lacrimal canaliculus of a human eye, with the head and body anchored by the punctum. When so inserted (in accord with technique well known in the art), the medication is released from the plug to the ocular surface over time at the predetermined rate to provide medicinal or therapeutic benefit.

Figure 6:
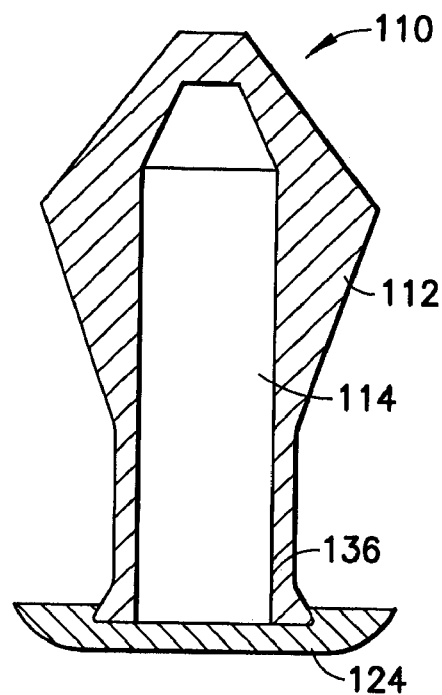
FIGS. 6 and 7 illustrate a method of manufacturing a second embodiment of a punctum plug according to the invention.
Figure 7:
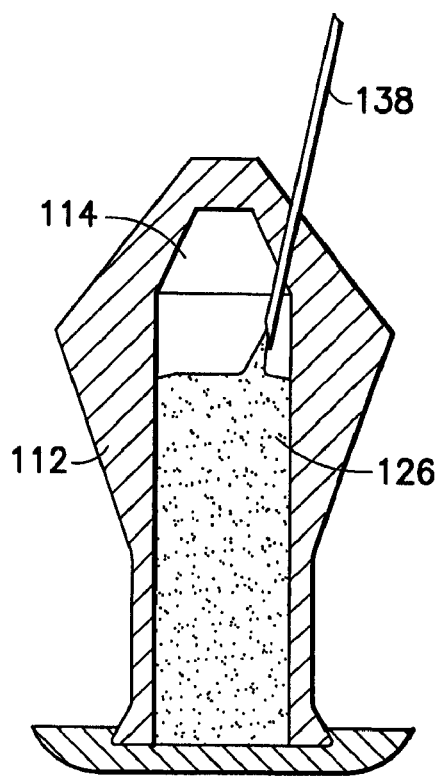

Turning now to FIGS. 6 and 7, a second method of manufacturing a plug 110 according to the invention is shown. The body 112 of the plug is made from a self-healing material, with an internal space 114 open only at the neck end 136. The head 124 is then attached to the body 112 prior to filing the reservoir space 114 with medication. A needle 138 or similar device is punctured through the body 112 to inject the medication 126. After injecting the medication 126, the needle 138 is withdrawn, with the body self-healing to retain the medication 126.

Figure 8:
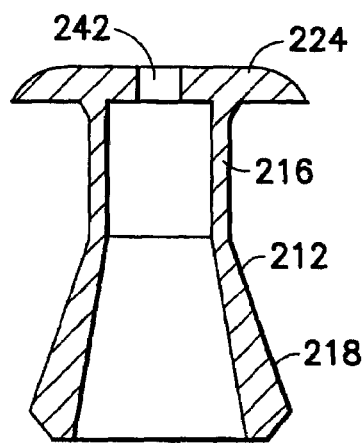
FIGS. 8 through 10 illustrate a method of manufacturing a third embodiment of a punctum plug according to the invention.
Figure 9:
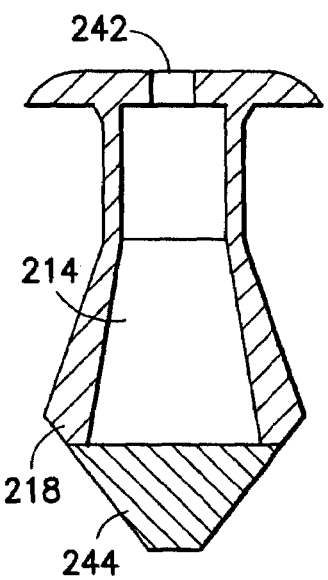
Figure 10:
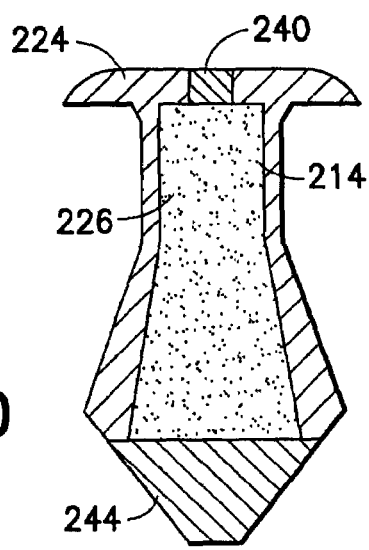

In accord with yet another embodiment of the invention a plug 210 (FIG. 10) is provided adapted to release medication into the lacrimal duct, e.g., allergy, sinus or throat medications, rather than to the surface of the eye. Referring to FIG. 8, the body 212 is molded of the first relatively impermeable material with head 224, neck 216 and a flared open end 218. The head portion 224 defines an opening 242. Referring to FIG. 9, a tip 244 of a second relatively more permeable material is molded onto the flared open end 218 to define a reservoir within the body 212 and preferably a portion of the tip 244. Medication 226 is injected through the opening 242 into the reservoir 214. Referring to FIG. 10, finally, a stopper 240 is provided in the opening in the head portion to close the reservoir 214. This embodiment may also be designed without a seal; i.e., in the manner of using a self-healing body material, as described above.

Figure 11:
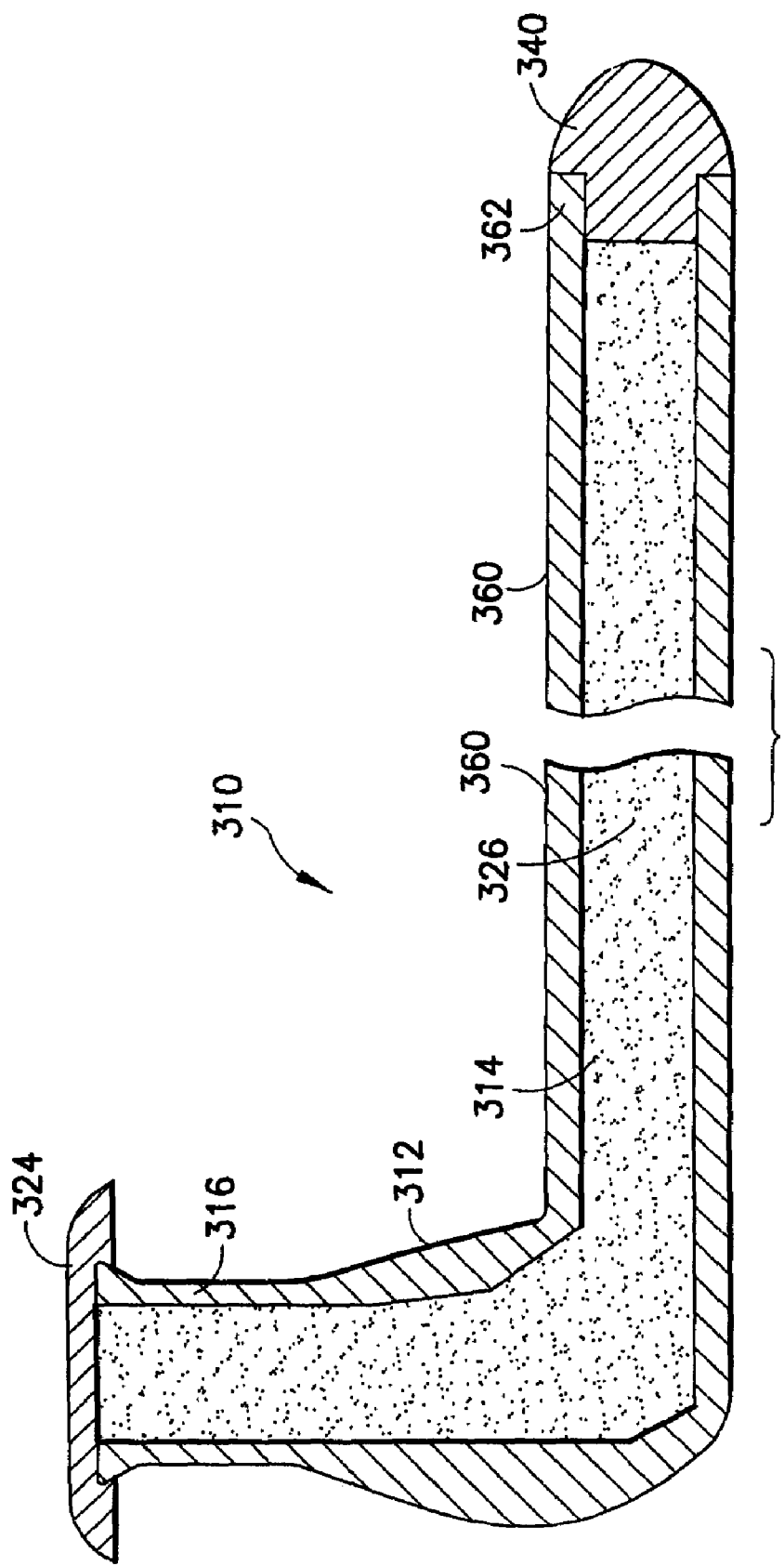
FIG. 11 is a schematic section view of a monocanalicular insert according to another embodiment of the invention.

Turning now to FIG. 11, another design of a lacrimal insert 310 is shown. The insert 310 shown may be manufactured in accord with any of the methods described above to release medication at the head end or tip end. By of example, as shown, the insert 310 is manufactured with a body 312 having an elongate distal tubular portion 360 preferably angled relative to a neck 316 of the body. The body 312 and tubing portion 360 define a reservoir 314 of substantially greater volume than in the other embodiments. After molding the body 312 of a first relatively impermeable material, the head 324 is molded onto the neck 316 of the body 312 of a second relatively permeable material. Medication 326 is provided in the reservoir through the open end 362 of the tubular portion 360 and a preferably medication-impermeable stopper element 340 is used to close the reservoir 314.

It will be appreciated that in accord with the invention, the portion of the insert at which the medication is released is precisely fabricated in order to control release of the medication, and the reservoir is filled and then closed away from the area of permeability.

While thus far the invention has been described with respect to lacrimal applications, it is appreciated that implantable devices having medication-storing reservoirs made in accord with the above principles and methodology can be applied to other applications. For example, the insert can be adapted in size and shape for insertion into an opening in a cochlea to deliver a medication to the inner ear. By way of another example, the insert can be implanted into a hole drilled in bone to deliver a medication or therapeutic into the medullary canal, including a gene-therapeutic agent. In accord with yet another example, an insert can be implanted into a hole drilled into the skull to deliver neurological medications to the brain. In yet another example, an insert can be anchored at a surgical opening to deliver a medication such as an antibiotic directly to a surgical site. The inserts may also be implanted within the nasal cavity. Such inserts may be of various shapes, sizes and first and second materials, each suitable for its particular application. Furthermore, the devices may be adapted in size and shape for veterinary applications, particularly for, though not limited to, mammals. In each application, the insert preferably includes a flared or barbed structure or other means for anchoring the insert in the body opening.

There have been described and illustrated herein several embodiments of inserts, and particularly several lacrimal inserts, adapted to release medication over time and methods of manufacturing such inserts. While particular embodiments of the invention have been described, it is not intended that the invention be limited thereto, as it is intended that the invention be as broad in scope as the art will allow and that the specification be read likewise. Thus, while exemplar shapes have been shown with respect to the inserts, it will be appreciated that other suitable shapes for the inserts, particularly those known in the art for similar inserts which do not release medications in a manner as described or which are not formed in a manner as described, may be used as well. It will therefore be appreciated by those skilled in the art that yet other modifications could be made to the provided invention without deviating from its scope as claimed.

What is claimed is:

1. A method of manufacturing a lacrimal insert, comprising:
   a) molding a lacrimal insert sized for insertion into the lacrimal punctum, the insert having an internal medication-storing reservoir bounded and defined by separate materials which are respectively relatively permeable and impermeable to the medication; and
   b) injecting the medication into the reservoir at a location spaced apart from the permeable material.

2. A method according to claim 1, further comprising: sealing the insert at the location at which the medication is injected.

3. A method according to claim 1, wherein: said molding includes molding the insert from two different silicones, one of which is permeable to the medication and the other of which is relatively impermeable to the medication.

4. A method of manufacturing a lacrimal insert, comprising:
   a) providing a body of the lacrimal insert sized for insertion into the lacrimal punctum, the body of the insert having neck and tip ends, and defining an internal space which is open at both the neck and tip ends, the body being made from a first material;
   b) providing a head of the insert onto the neck end of the body to partially enclose the internal space and define a reservoir, the head being made from a second material;
   c) injecting medication into the reservoir of the insert through the tip end of the body; and
   d) sealing the tip end of the body closed,
wherein the first material is relatively impermeable to the medication and the second material is relatively permeable to the medication so as to release the medication through the head of the insert at a determinable rate.

5. A method according to claim 4, wherein: said providing the head of the insert onto the neck end of the body includes molding the head of the insert onto the neck end of the body.

6. A method according to claim 5, wherein: said head is molded onto said neck end of said body after the body is formed.

7. A method according to claim 4, wherein: said first and second materials are different silicones.

8. A method according to claim 4, wherein: said sealing includes providing a stopper element in the open tip end after said injecting.

9. A method of manufacturing a lacrimal insert, comprising:
   a) providing a body of the lacrimal insert sized for insertion into the lacrimal punctum, the body of the insert having head, neck and open end, and defining an internal space and an opening in the head, the body made from a first material;
   b) providing a tip of the insert onto the open end of the body to partially enclose the internal space and define a reservoir, the tip made from a second material;
   c) injecting medication into the reservoir of the insert through the opening in the head of the body; and
   d) sealing the opening in the head of the body closed,
wherein the first material is relatively impermeable to the medication and the second material is relatively permeable to the medication so as to release the medication through the head of the insert at a determinable rate.

10. A method according to claim 9, wherein: said providing the tip of the insert onto the open end of the body includes molding the tip of the insert onto the open end of the body.

11. A method according to claim 9, wherein: said first and second materials are different silicones.

12. A method according to claim 9, wherein: said sealing includes providing a stopper element in the opening in the head after said injecting.

* * * * *